(12) United States Patent
Sayadi et al.

(10) Patent No.: US 8,862,144 B2
(45) Date of Patent: Oct. 14, 2014

(54) METHOD FOR MANAGING A WIRELESS TELECOMMUNICATION NETWORK

(75) Inventors: Bessem Sayadi, Nozay (FR); Afef Feki, Nozay (FR)

(73) Assignee: Alcatel Lucent, Boulogne Billancourt (FR)

( * ) Notice: Subject to any disclaimer, the term of this patent is extended or adjusted under 35 U.S.C. 154(b) by 0 days.

(21) Appl. No.: 13/704,796

(22) PCT Filed: May 9, 2011

(86) PCT No.: PCT/EP2011/057413
§ 371 (c)(1), (2), (4) Date: Dec. 17, 2012

(87) PCT Pub. No.: WO2011/157486
PCT Pub. Date: Dec. 22, 2011

(65) Prior Publication Data
US 2013/0095844 A1    Apr. 18, 2013

(30) Foreign Application Priority Data

Jun. 17, 2010    (EP) .................................... 10166410

(51) Int. Cl.
*H04W 40/00*    (2009.01)
*H04W 72/00*    (2009.01)
*C12N 15/81*    (2006.01)
*H04W 72/08*    (2009.01)
*H04W 28/18*    (2009.01)
*H04W 92/12*    (2009.01)
*H04W 92/04*    (2009.01)

(52) U.S. Cl.
CPC .............. *C12N 15/815* (2013.01); *C12N 15/81* (2013.01); *H04W 92/12* (2013.01); *H04W 72/08* (2013.01); *H04W 28/18* (2013.01); *H04W 92/045* (2013.01)
USPC ...... 455/452.2; 455/449; 455/450; 455/452.1

(58) Field of Classification Search
USPC .................................................. 455/446–454
See application file for complete search history.

(56) References Cited

U.S. PATENT DOCUMENTS 7,855,977 B2 * 12/2010 Morrison et al. ............. 370/252
8,126,476 B2 *  2/2012 Vardi et al. .................. 455/456.1

(Continued)

FOREIGN PATENT DOCUMENTS

| EP | 2 081 324 A1 | 7/2009 |
| GB | 2 452 794 A | 3/2009 |
| WO | WO 2009/131898 A1 | 10/2009 |

OTHER PUBLICATIONS

J. Olmos et al., "A Functional End-to-End QoS Architecture Enabling Radio and IP Transport Coordination," IEEE Wireless Communications and Networking Conference, IEEE Operations Center, XP031097931, pp. 4348-4353, Mar. 1, 2007.

(Continued)

*Primary Examiner* — Nathan Mitchell
(74) *Attorney, Agent, or Firm* — Fay Sharpe LLP

(57) ABSTRACT

The invention relates to a method for managing cells (100*i*, 100*j*) of a telecommunication network (102), said cells (100*i*, 100*j*) being supported by radio base stations (104*i*, 104*j*) aimed to provide wireless communication support to mobile terminals ((106*i*) connected to said communication network (102), each radio base station (104*i*, 104*j*) being linked to a core (108) of the telecommunication network through an associated backhaul (105*i*, 104*j*), characterized in that it comprises the step of managing dynamically communications resources of the telecommunication base stations by considering a dynamical backhaul quality BQ parameter for each base station (104*i*, 104*j*) and comparing different backhaul quality BQ parameters of different base stations (104*i*, 104*j*) in order to optimize the communication resources operations of the telecommunication network (102).

10 Claims, 2 Drawing Sheets

(56) References Cited

U.S. PATENT DOCUMENTS

Figure 5:
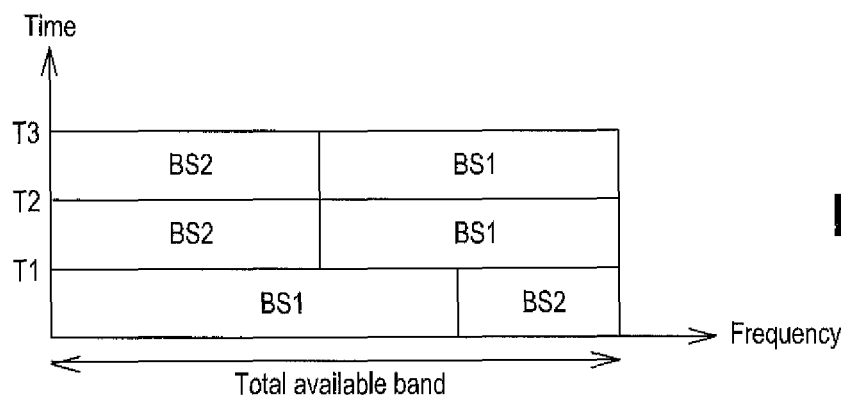

| | | |
|---|---|---|
| 2007/0177510 A1 | 8/2007 | Natarajan et al. |
| 2008/0248807 A1 | 10/2008 | Kim et al. |
| 2009/0180428 A1* | 7/2009 | Viswanath .................... 370/328 |
| 2009/0213825 A1* | 8/2009 | Gupta et al. .................. 370/338 |
| 2009/0264123 A1* | 10/2009 | Agashe et al. ................ 455/434 |
| 2010/0034078 A1 | 2/2010 | Jia et al. |
| 2010/0165857 A1* | 7/2010 | Meylan et al. ................ 370/252 |
| 2012/0231806 A1* | 9/2012 | Maric et al. ................ 455/452.2 |
| 2013/0090121 A1* | 4/2013 | Zhang et al. .................. 455/450 |

OTHER PUBLICATIONS

International Search Report for PCT/EP2011/057413 dated Jun. 28, 2011.
Notice of Reason for Refusal for corresponding Japanese Patent Application No. 2013-514610, dated Jan. 28, 2014, 7 pages.
Notice of Preliminary Rejection for corresponding Korean Patent Application No. 10-2013-7000907, dated Feb. 25, 2014, 8 pages.

* cited by examiner

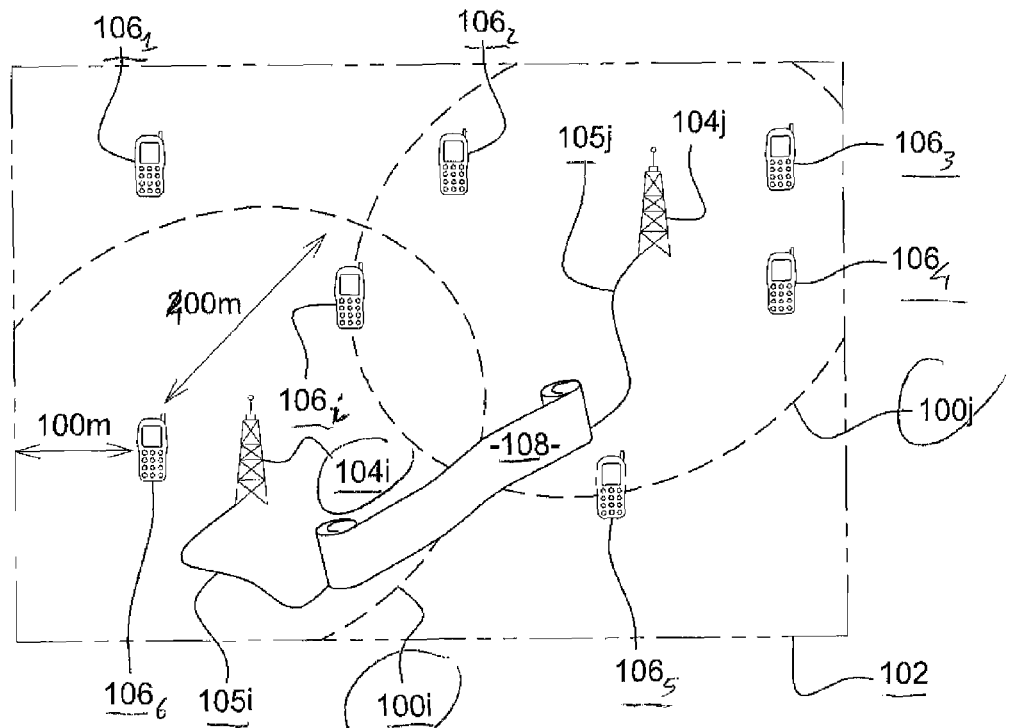
Fig. 1
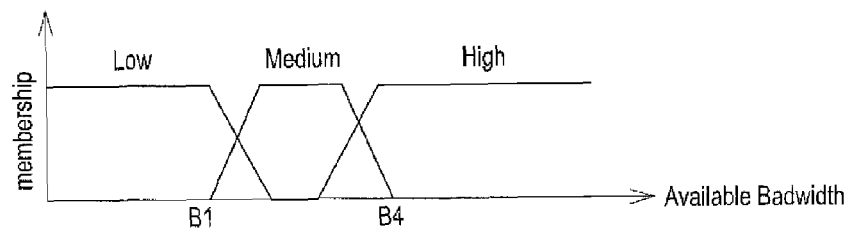
Fig. 2
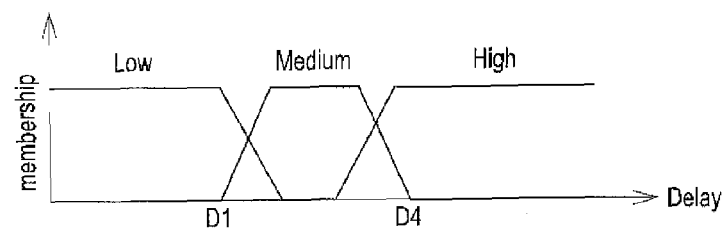
Fig. 3
| Bandwidth \ Delay | Low | Medium | High |
|---|---|---|---|
| Low | 1 | 0 | 0 |
| Medium | 2 | 1 | 0 |
| High | 3 | 2 | 1 |
Fig. 4

METHOD FOR MANAGING A WIRELESS TELECOMMUNICATION NETWORK

The present invention relates to a method for managing a wireless telecommunication network.

Telecommunication operators develop their network management in order to ensure high quality of service and high data rates to their end users. For that purpose, small cells networks are increasingly used since such small cells—i.e. cells of a size generally comprise between 100 or 200 m—are interesting for delivering high per-user data rates, uniformly across a coverage area, while providing greater overall throughput via higher spatial reuse.

In addition, a small cells network can be operated in both an indoor and an outdoor environment which allows, for instance, a continuity of service between an indoor area and an outdoor area.

Since communication resources of a small cells telecommunication network are shared between said small cells, it is primordial to share efficiently said available radio resources among the small cells of the network. In other words, the employed resource allocation procedure highly impacts the performance of the overall communication network.

One of the main issues when deploying small cells communication networks is to guarantee a continuity of service and an efficient handover between neighboring cells, a "neighboring cell" being a cell which is adjacent or proximate to the considered cell. For that purpose, a neighboring cell list (NCL) is set by each cell in order to identify different neighboring cells that can be seen (captured or received) by the terminal and responding to a set of predefined criteria (mainly the level of received signal), a communication handover being possible for a terminal communication from the cell owning the list to a cell listed thereon.

The optimization of said neighbor cell list (NCL) is a crucial issue that targets to provide seamless mobility and satisfactory quality of end user experience. As reflected by the publication of David Soldani and Ivan Ore, "Self-optimizing neighbor cell list for UTRA FDD networks using detected set reporting", published in IEEE 65th Vehicular Technology Conference, 2007. VTC2007-Spring, it is known to consider an efficient optimization procedure of the Neighbor Cell List establishment mainly on the radio communication quality indicators.

The invention results from the finding that the small cells are supported by base stations whose backhauling connection to the core communication network—i.e. the wired connection between the radio base station and the telecommunication network—should be taken into account for sharing the communication resources sharing among the different small cells.

More precisely the invention results from the finding that the quality of a base station backhauling should be considered in the distribution of the telecommunication network resources, for instance to establish NCLs or distribute radio frequencies between base stations.

Indeed, a small cell base station can be connected with different types of backhauling, for instance depending on the base station location, to the core network, such as an optical fiber connection, a Digital Subscriber Line connection, a power transmission line and/or a cooper line, each one of said connection having its own particularities to be considered in order to improve the telecommunication network operations.

Thus, the invention relates to a method for managing cells of a telecommunication network, said cells being supported by radio base stations aimed to provide wireless communication support to mobile terminals connected to said communication network, each radio base station being linked to a core of the telecommunication network through an associate backhaul, characterized in that it comprises the step of managing dynamically communications resources of the telecommunication base stations by considering a dynamical backhaul quality parameter for each base station and comparing different backhaul quality parameters of different base stations in order to optimize the communication resources operations of the telecommunication network.

By implementing the invention, a telecommunication network can be managed in order to consider the backhaul operating conditions, so that the overall telecommunication network operation can be optimized.

In one embodiment, each cell is a small cell that does not cover an area which extends further to 400 meters from the base station, typically no further than 200 to 100 meters.

In one embodiment, the communications resources are managed by setting a neighboring cell list NCL, for each base station, which takes into account the dynamical backhauling quality BQ parameter of the neighboring cells considered into said list.

In one embodiment, the backhauling quality BQ parameter is considered to set the neighboring cell list NCL simultaneously to at least one of the following other parameters: a received signal quality SQ, a minimum bandwidth BM radio parameter, a requirement of service parameter. In one embodiment a score S is determined for each base station on the basis of a function F such as:

$$S = SQ \times F(\min(MB, BQ), \text{Quality of Service requirement})$$

So that the score of each base station considers the data rate transmission limit fixed by either the wireless part or the backhauling part of the considered base station.

In one embodiment the quality of service QS parameter is an indicator which varies according to the nature of the data to be transferred in a communication established by a terminal.

In one embodiment the communication resources are managed by setting the distribution of the network resources distribution between base stations by selecting radio ranges for each base station depending on the dynamic backhauling BQ parameter.

In one embodiment the radio ranges relate to frequencies allocated to a base station.

The invention also relates to a radio base station aimed to provide wireless communication support to mobile terminals connected to a communication network based on cells, said radio base station being linked to a core of the telecommunication network through an associate backhaul, characterized in that it comprises means to manage dynamically communications resources of the telecommunication base stations by considering a dynamical backhaul quality BQ parameter for each base station and comparing different backhaul quality BQ parameters of different base stations in order to optimize the communication resources operations of the telecommunication network following a method according to any of the previous embodiments.

The invention also concerns telecommunication network based on cells supported by radio base stations aimed to provide wireless communication support to mobile terminals connected to said communication network, each radio base station being linked to a core of the telecommunication network through an associate backhaul, characterized in that it comprises means to manage dynamically communications resources of the telecommunication base stations by considering a dynamical backhaul quality parameter for each base station and comparing different backhaul quality BQ parameters of different base stations in order to optimize the communication following a method according to any of the previous embodiments.

Figure 6:
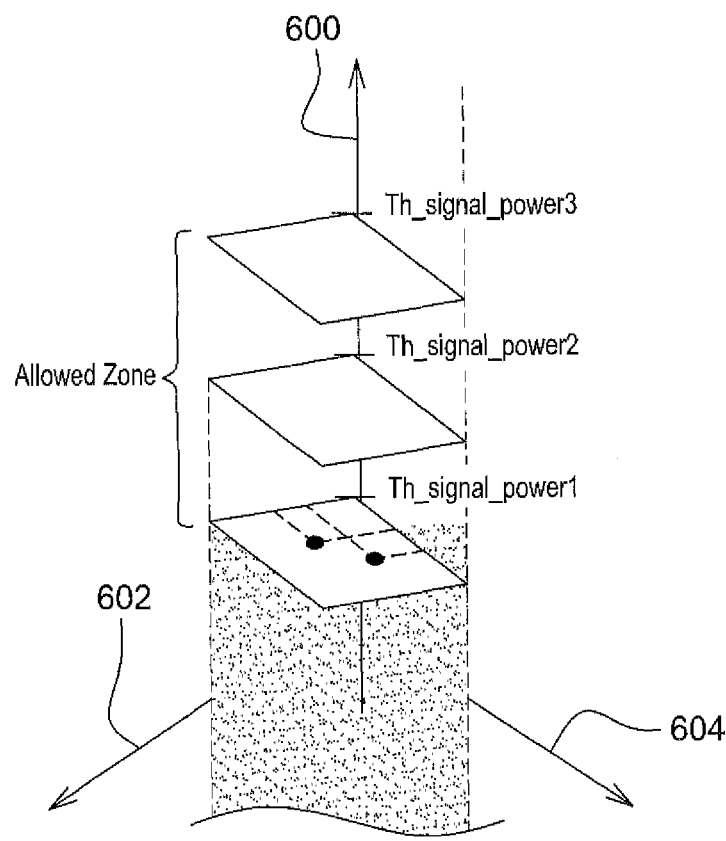

The accompanying drawings are included to provide a further understanding of the invention and are incorporated in and constitute a part of this specification, to illustrate embodiments of the invention and, together with the description, to explain the principles of the invention whose scope is defined by the claims and not limited by the description wherein:

FIG. 1 is a schematic view of a telecommunication network according to the invention, FIGS. 2 and 3 are diagrams of an assessment of a base station assessment according to one embodiment of the invention, FIG. 4 is a table of an assessment of a base station assessment according to one embodiment of the invention, FIG. 5 is a diagram representing a possible distribution of frequency distribution among different interfering base stations, and FIG. 6 depicts a graphical distribution of resources in a telecommunication network according to the invention.

Reference will now be made in detail to the present preferred embodiment of the invention, an example of which is illustrated in the accompanying drawings. Wherever possible, the same reference numerals will be used throughout the drawings to refer to the same or like parts.

In reference to FIG. 1, the invention relates to a method for managing small cells $100i$ of a telecommunication network $102$, each small cell $100i$ being supported by a radio base station $104i$ aimed to provide wireless/radio communication support to mobile terminals $106i$ connected to said telecommunication network $102$.

Each small cell covers an area which does not extend further to 200 meters from the base station, typically no further to 100 meters, and each base station $104i$ is linked to a core $106$ of the telecommunication network $102$ through an associate backhauling wired connection $105i$ whose nature might vary from one base station to another. For instance, a backhaul might use a connection based on an optical fiber, a digital subscriber line, a cooper line or a power transmission line.

According to the invention, the telecommunication network comprises means to manage dynamically communication resources of the telecommunication base stations by considering a dynamic backhauling quality BQ parameter for each base station and comparing different BQ parameters of different base stations in order to optimize the communication resources operations of the telecommunication network.

In a first embodiment, the communications resources are managed when setting a neighboring cell list (NCL) either by a base station or by a base station or by a terminal depending o the network so that said NCL setting takes into account the dynamic BQ parameter of the neighboring cells considered into said list.

Indeed, as already explained, in mobile communications networks, the base stations $104i$ are deployed to connect user terminals $106i$ to a wireless network. Each user terminal is initially connected to a base station when it is located within the cell area served by the base station. Nevertheless, due to mobility or when the base station experiences congestion, the user terminal communication is handed off to a different base station which is selected from the Neighboring Cell List (NCL).

In other words, the NCL identifies the different cells declared by the terminal as valid (according to preset criteria such as the minimum received power) whereto a handover is possible from the cell owning the list to the cell listed. But since backhaul are different or heterogeneous, the backhaul $105i$ of a base station $104i$ might be more limited or congested as compared to other another base station $104j$ backhauling $105j$. Thus, the handover of telecommunication should consider the availability and the occupancy of the neighboring cells backhauls to be optimized.

Also, a user terminal should select a base station by taking into account important parameters such as:

The received signal quality,

The real offered bandwidth by comparing the available wireless bandwidth and the available backhaul bandwidth, The requirement of its service (Quality of service). Typically the delay is the more important feature.

For that purpose, each mobile terminal $106$ might take select a base station by considering the above mentioned three parameters through a score S which depends on:

A received signal quality parameter SQ as the signal power. For instance, said SQ parameter could be considered as per-interval function wherein SQ equals:

0 if the received signal of the target cell is above a threshold1.

1 if the received signal of the target cell is between threshold1 and a threshold2.

2 if the received signal of the target cell is between threshold2 and a threshold3.

A measured minimum bandwidth MB between the wireless segment and the backhaul. For instance, said MB parameter could be considered through a membership function of the available bandwidth as depicted in FIG. 2. More precisely, by defining some thresholds (B1.B4), the available bandwidth could be qualified as low, medium or high depending on the requirement of the service searched by the terminal. For instance, for real time traffic, a minimum bandwidth depending on the requested resolution is required whereas, for example, a high bandwidth is required to ensure a high quality for a CIF format.

A delay D of data transmission between the base station and the core network, typically due to a buffering period when the backhaul is congested.

As for the bandwidth parameter, the delay D could be qualified as low, medium or high depending (FIG. 3) on the requirement of the service and through some thresholds (D1.D4). For instance, the delay is not a stringent requirement for a HTTP (for Hyper Text Transfer Protocol) traffic so that its service could be performed through the low, the medium or the high region.

In one embodiment wherein it is consider that the received signal quality indicator is the more important parameter, the score function is split up into two parts as the following:

$$S=SQ \times F(\min(MB,BQ), \text{Quality of Service requirement})$$

Wherein the "quality of service parameter" is an indicator which varies according to the service required by the terminal. For instance, considering two users requiring, for one, a web service (http) and, for the other, a real time traffic, it is known that the http traffic tolerate a large delay so that, even when a base station backhauling is congested, the terminal should be connected to the cell offering the best radio connectivity while the terminal requiring real time traffic (e.g. mobile TV), which is delay dependent, should be connected to a cell having a non congested backhaul.

The score S is assigned to each cell, for instance through a table as represented in FIG. 4 relating to the MB and BQ parameters, and it is upon its values that the ranking of the neighbor cells list is realized so that the terminal tends to select the cell having the higher score number.

After computing the score of the different received cells (declared eligible by comparing their received signals to the defined thresholds, the indicator function), it selects the cell having a score different from 0.

According to another embodiment of the invention, the backhaul quality parameter is required for the distribution of resources between different base stations independently of the neighboring cell list establishment.

Indeed, the telecommunication network resources should first be allocated and shared between the different small cells and this issue appears to be more critical in the case of a small cells network where the number of interfering cells is high (due to high density and low coverage area).

Considering the two base station BS1 104$i$ and BS2 104$j$ of FIG. 1, respectively connected to the backhauls Bh1 105$i$ and Bh2 105$j$, they may operate in the same band and interfere (low separating distance).

In this case, there is a need that each base station 104$i$ and 104$j$ selects its radio resources in the way that the overall generated interference is minimized, as depicted for instance in FIG. 5. At each period Tk, a part of the total available frequency band is allocated to a given cell. In the prior art, the resource allocation procedure is performed on the basis of:
  the total available band,
  the needs of each base stations, generally deduced from the number of attached users and the type of service/traffic,
  the usage/needs of the neighboring cells, Thus, the resource allocation procedure of the prior art takes into account only the wireless link characteristics. Nevertheless, this method can be proved to be weak in the case of heterogeneous/various backhaul connection of each involved base station.

For example, a given conventional resource allocation procedure can be applied at a time t and will continue for a duration T, resulting in a first average data rate DR1 for the base station BS1 104$i$ and an average data rate DR2 for the base station BS2 104$j$.

If at an instant the backhaul connection of the base station BS1 104$i$ allows an average data rate DR_Bh1 inferior the previous average DR1, the effective average data rate of the base station BS1 104$i$ to be considered is DR_Bh1.

The different base stations determine the backhaul characteristics either with a probing based on TCP principle (to fix the bandwidth) or by operator configurations. One way to sent backhaul information occupancy is to use the common channels to the users.

To summarize, the invention discloses the consideration of a backhaul quality (BQ) parameter in combination with other parameters, such as a typical delay parameter, in order to optimize the distribution of communication resources within a telecommunication network.

The invention can be implemented through an unlimited number of embodiments and functions. For instance, by coupling the two parameters, a terminal could select an appropriate target cell offering a quality of service adapted to said parameter while a load equilibrium between the cells could be achieved in the communication network.

Indeed, by exploiting classically only the radio information, all the user terminals tend to select the same cell i.e. the best candidate while, thanks to the invention, the users tend to select the appropriate cell offering them a required quality of service at the base station backhauling level, as depicted in FIG. 6 which represents three parameters to be considered for a cell selection. In an allowed zone, at a certain level of received signal (axis 600) should be based on an acceptable combination of delay (axis 602) and available transmission rate (axis 604), which is limited by the minimum bandwidth of the backhaul or the wireless segment.

The invention can also be implemented according to different embodiments regardless of the network topology and type (macro, femto cells . . . ) despite the fact that the description focus on the example of small cells network where the heterogeneity of backhaul is most explicit.

The invention claimed is:

1. Method for managing cells of a telecommunication network, said cells being supported by radio base stations aimed to provide wireless communication support to mobile terminals connected to said communication network, each radio base station being linked to a core of the telecommunication network through an associated backhaul, wherein the method comprises dynamically distributing communications resources among the telecommunication base stations by considering a dynamical backhaul quality BQ parameter for each base station and comparing different backhaul quality BQ parameters of different base stations in order to optimize the communication resources operations of the telecommunication network.

2. Method according to claim 1 wherein each cell is a small cell that does not cover an area which extends further than 400 meters from the base station.

3. Method according to claim 1 wherein the communications resources are managed by setting a neighboring cell list NCL for each base station which takes into account the dynamical backhauling quality BQ parameter of the neighboring cells considered into said list.

4. Method according to claim 3 wherein the backhauling quality parameter is considered to set the neighboring cell list simultaneously to at least one of the following other parameters: a received signal quality, a minimum bandwidth radio parameter, a requirement of service parameter.

5. Method according to claim 4 wherein a score S is determined for each base station on the basis of a function F such as:

$$S=SQ \times F(\min(MB,BQ), \text{Quality of Service requirement})$$

where SQ is a signal quality parameter, and wherein the score of each base station considers the data rate transmission limit fixed by either the wireless part or the backhauling part of the considered base station.

6. Method according to claim 5 wherein the quality of service QS parameter is an indicator which varies according to the nature of the data to be transferred in a communication established by a terminal.

7. Method according to claim 1 wherein the communication resources are managed by setting the distribution of the network resources distribution between base stations by selecting radio ranges for each base station depending on the dynamic backhauling quality BQ parameter of each base station.

8. Method according to claim 7 wherein the radio ranges relate to frequencies allocated to a base station.

9. Radio base station aimed to provide wireless communication support to mobile terminals connected to a communication network based on cells, said radio base station being linked to a core of the telecommunication network through an associate backhaul, wherein the station comprises means to manage dynamically communications resources of the telecommunication base stations by considering a dynamical backhaul quality BQ parameter for each base station and comparing different backhaul quality BQ parameters of different base stations in order to optimize the communication resources operations of the telecommunication network following a method according to claim 1.

10. Telecommunication network based on cells supported by radio base stations aimed to provide wireless communication support to mobile terminals connected to said communication network, each radio base station being linked to a core of the telecommunication network through an associate backhaul, wherein the network comprises means to manage dynamically communications resources of the telecommunication base stations by considering a dynamical backhaul quality parameter for each base station and comparing different backhaul quality BQ parameters of different base stations in order to optimize the communication following a method according to claim 1.

* * * * *